United States Patent [19]

Sarnoff et al.

[11] 3,938,507
[45] Feb. 17, 1976

[54] PORTABLE HEART MONITOR

[75] Inventors: Stanley J. Sarnoff, Bethesda; Herbert E. Reinhold, Jr.; Allan M. Wolfe, both of Rockville, all of Md.

[73] Assignee: Survival Technology Incorporated, Bethesda, Md.

[22] Filed: Nov. 1, 1973

[21] Appl. No.: 411,843

[52] U.S. Cl. ...... 128/2.06 B; 128/2.06 F; 128/2.1 A
[51] Int. Cl.² .......................................... A61B 5/04
[58] Field of Search ...... 128/2.05 P, 2.05 R, 2.05 S, 128/2.05 T, 2.06 A, 2.06 B, 2.06 E, 2.06 F, 2.06 R, 2.1 A, 2.1 R, 419 P

[56] References Cited
UNITED STATES PATENTS

| | | | |
|---|---|---|---|
| 3,135,264 | 6/1964 | Tischler | 128/2.06 A |
| 3,144,019 | 8/1964 | Haber | 128/2.06 A |
| 3,160,708 | 12/1964 | Andries et al. | 128/2.05 S |
| 3,228,391 | 1/1966 | Fitler et al. | 128/2.05 T |
| 3,352,300 | 11/1967 | Rose | 128/2.06 A |
| 3,491,750 | 1/1970 | King | 128/2.06 R |
| 3,524,442 | 8/1970 | Horth | 128/2.06 A |
| 3,598,128 | 8/1971 | Chardack | 128/419 P |
| 3,633,569 | 1/1972 | Brayshaw et al. | 128/2.06 A |
| 3,742,938 | 7/1973 | Stern | 128/2.05 T |
| 3,769,965 | 11/1973 | Raddi et al. | 128/2.05 R |
| 3,802,698 | 4/1974 | Burian et al. | 128/2.06 F |

*Primary Examiner*—William E. Kamm
*Attorney, Agent, or Firm*—Cushman, Darby & Cushman

[57] ABSTRACT

A portable heart monitoring apparatus incorporating unique structural and functional features. Electrodes carried on the apparatus capture electrical signals representing the functioning of a heart beating therewithin and provides sensible output indications corresponding to predetermined characteristics of the electrical signals and, hence, of the detected heartbeat. One of the sensible outputs provided is the selective actuation of either of two logic lights indicating whether the heartbeat is above or below respectively a predetermined beating rate. The unit is automatically turned on by merely holding the instrument in the user's hand and the selective actuation of the various operational modes may be conveniently made by selectively placing one of the hands's digits (such as the thumb) from one touch contact point to another. Part of the operation in the test mode involves the effective testing of the reserve battery power without actually loading the battery. Structurally, the device is convenient to hold in the hand and includes, on one side, a ground plane for establishing electrical contact with the user's hand. The ground plane structure is also formed as an open-sided storage compartment for the electrodes and is surrounded by a wrap-around structure for self-storing of the electrode leads.

32 Claims, 15 Drawing Figures

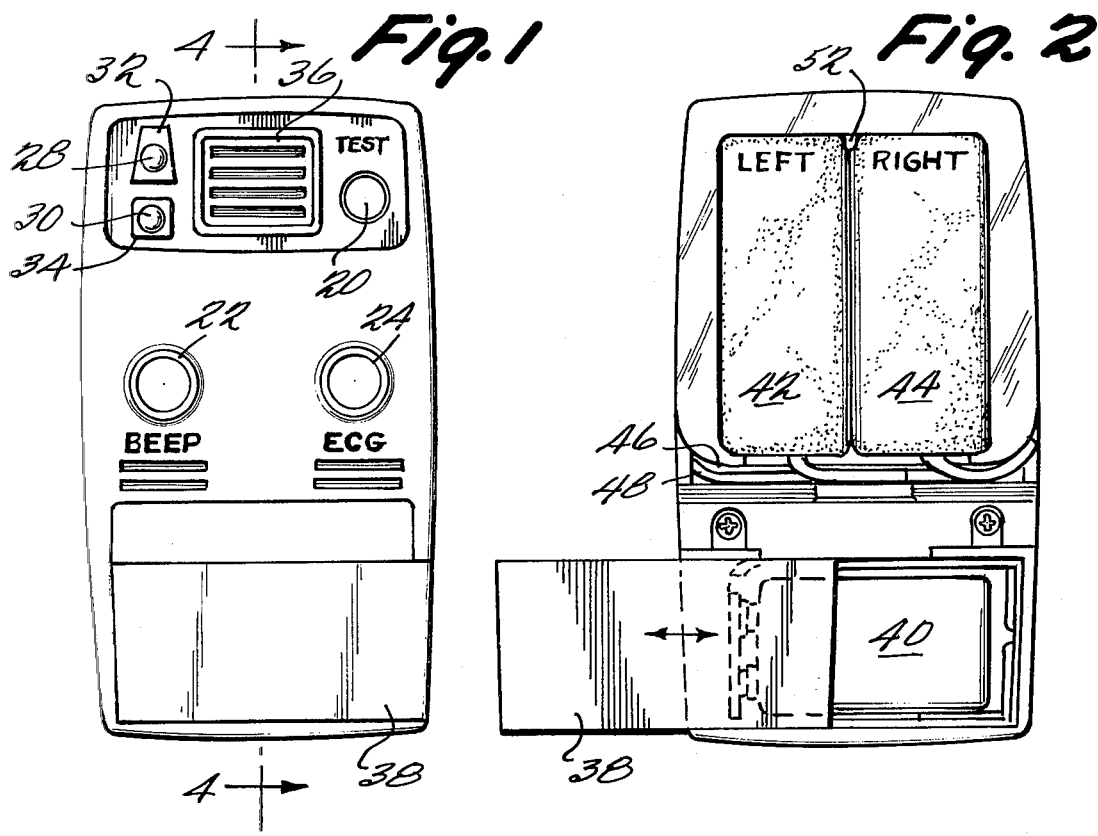
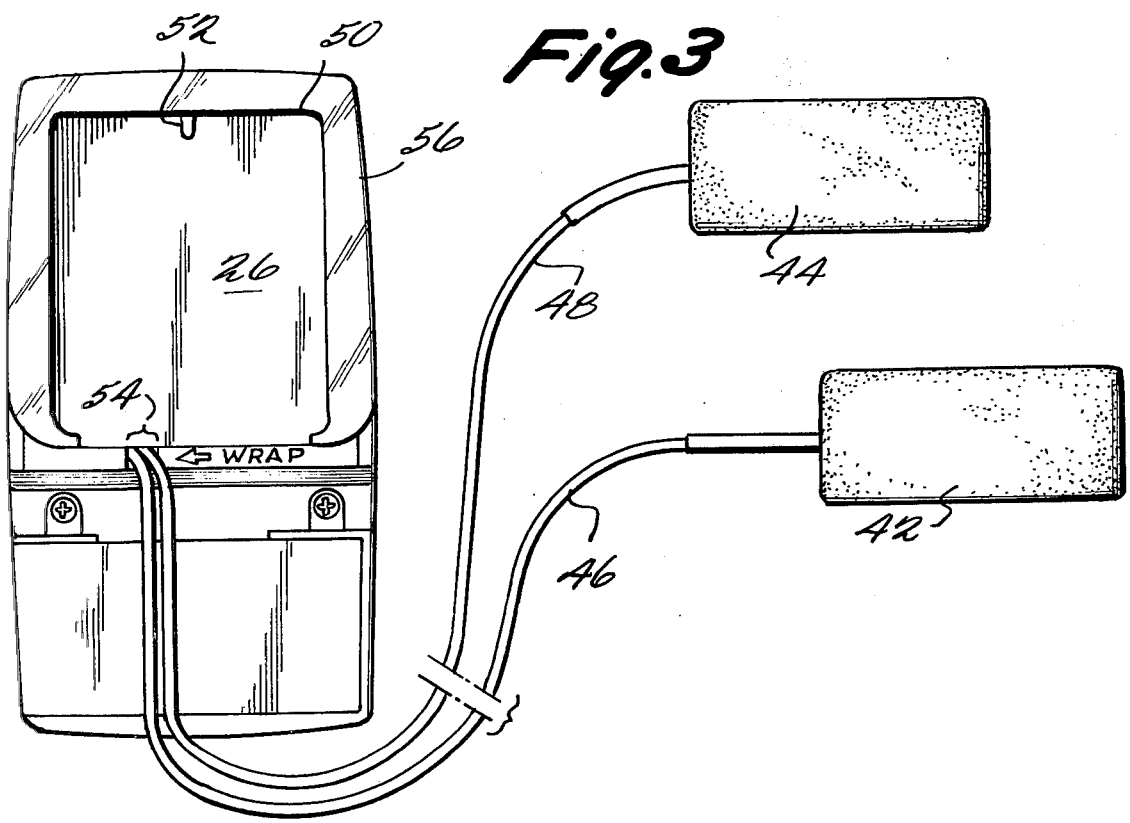

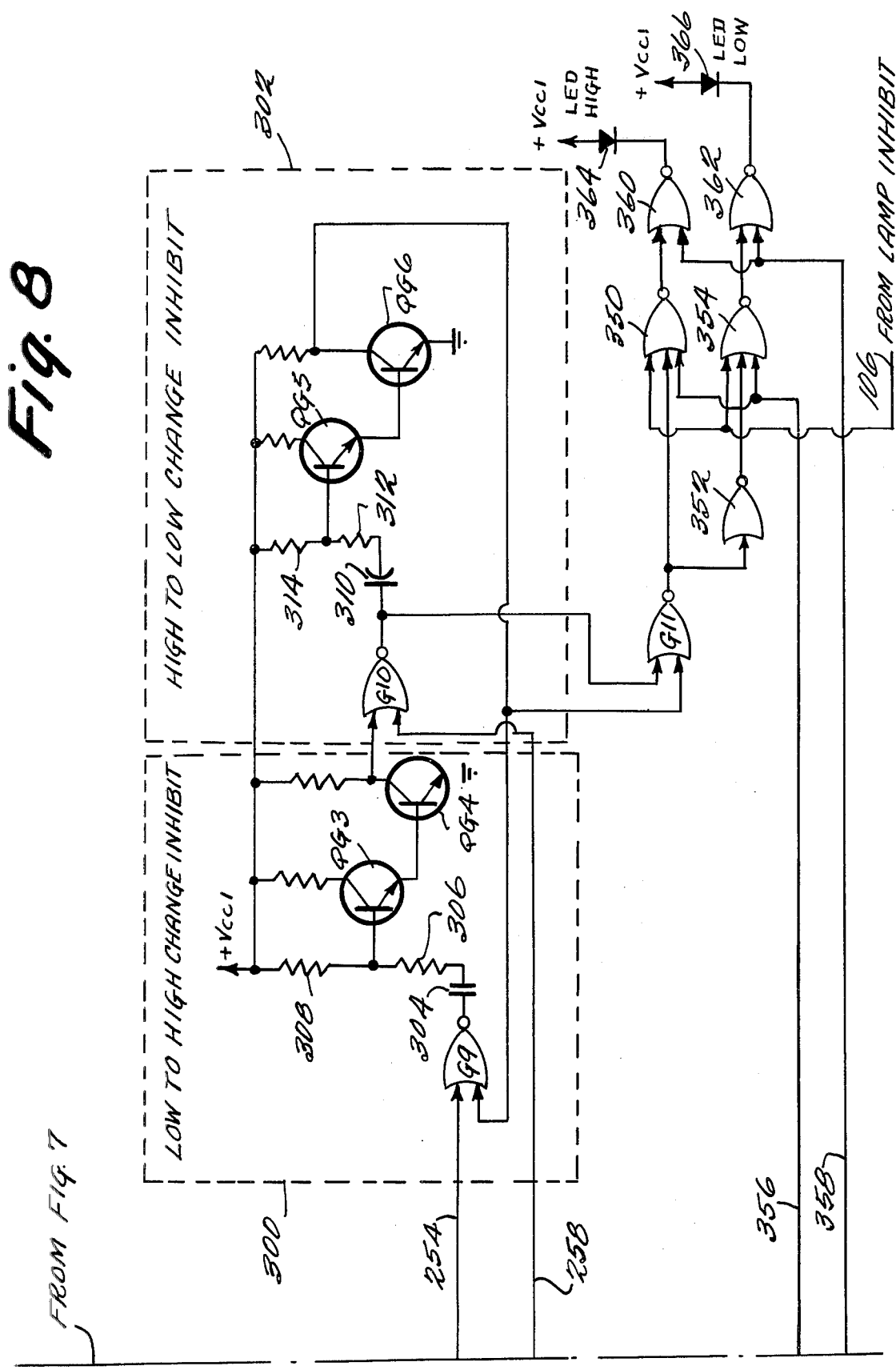

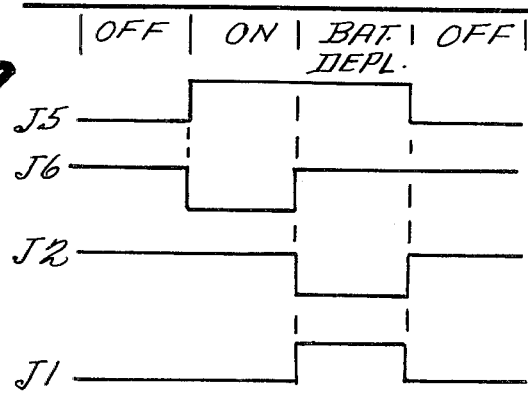
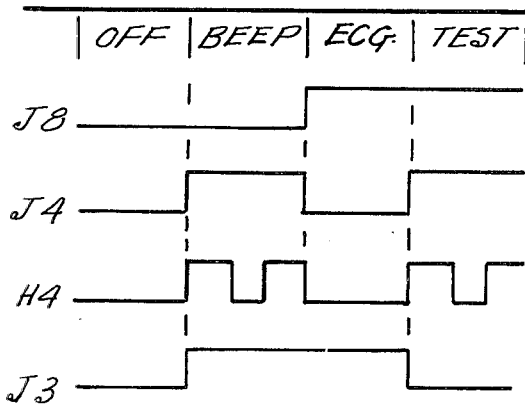
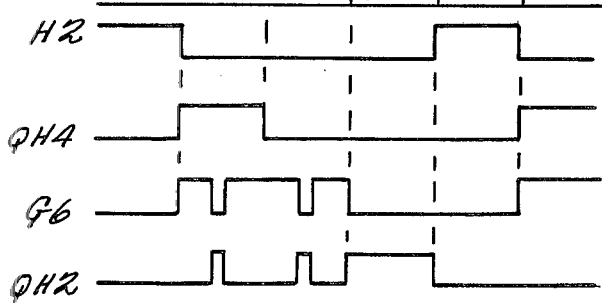

PORTABLE HEART MONITOR

This invention generally relates to portable heart monitoring apparatus. It is related to commonly assigned, co-pending U.S. application Ser. Nos. 55,647 filed July 17, 1970 now abandoned in favor of Ser. No. 296,841 filed Oct. 12, 1972 as a continuation of Ser. Nos. 55,647; 311,835 filed Dec. 4, 1972 now abandoned in favor of Ser. No. 488,434 filed July 15, 1974 as a continuation of Ser. No. 311,835 and Ser. No. 230,753 filed Mar. 1, 1972; now issued as U.S. Pat. No. 3,792,700 and the disclosures of all of which are hereby incorporated by reference.

The apparatus is particularly suited for use in the method of treating coronary prone individuals between the time that heart attack symptons occur and qualified direct contact personal care can be administered which is disclosed in commonly assigned Sarnoff application Ser. No. 311,835 filed Dec. 4, 1970 and its parent application Ser. No. 55,647 filed July 17, 1970.

Portable heart monitoring apparatus, in general, has been proposed before in the prior art. For instance, U.S. Pat. No. 3,613,670 - Edenhofer describes a pocket size self-contained cardiac monitor for on-patient or central station monitoring providing visible and/or audible signals related to the beat of the patient's heart. As those in the art will appreciate, there have been other attempts to provide a portable heart monitor to permit early cardiac diagnostic capabilities either by the patient himself and/or in conjunction with a central diagnostic center through which the patient can communicate by an ordinary telephone communication link. Some of the above referenced commonly assigned co-pending applications describe and claim various features of such methods and/or instruments that have been discovered and found to be particularly advantageous. Some of these features are incorporated in the exemplary embodiment to be described below.

However, in addition, the exemplary embodiment of heart monitoring apparatus to be discussed below is believed to include many novel and unique functions and/or structural features which make it a particularly advantageous improvement over any prior portable heart monitoring unit.

The overall exemplary embodiment comprises a small portable electrical circuit for monitoring the heart rate and/or electrocardiogram signal. Preferably, an electrode is placed under each armpit of the user to provide input electrical signals representing the functioning of the beating human heart to a high-gain electronics circuit including filtering devices for separating artifact and/or noise signals from the desired heart muscle signals. Heart rate information, per se, is output as audible beats and/or as the lighting of one of two "logic lamps" depending upon whether the heart rate is below or above some predetermined cross-over level, such as 60 beats per minute. The electrocardiogram information is frequency modulated via a voltage controlled oscillator to provide a variable frequency audio output. In either case, the heart rate information and/or the electrocardiogram information in audio form may be conveniently transmitted over a normal telephone communication link to a central diagnostic center by merely dialing the diagnostic center and holding the audio output portion of the instrument in the proximity of the telephone audio transmitter.

Since the first few heart rate measurements made by the electronic circuits may be erroneous due to the normal settling time of the electronics, etc., the exemplary embodiment to be described in more detail below incorporates a circuit for automaticaly suppressing all sensible output indications until sufficient time has passed to permit the electronics to settle down and provide reliable measurements. This may be accomplished by a simple timing circuit or by digital circuitry such as a counter which may count up to some predetermined number (e.g. 3–5) of the detected heartbeats before enabling the output circuitry.

Logic lights are arranged on one side of the instrument and the electrical circuitry attached thereto is adapted to cause one or the other of the logic lights to light depending upon whether the heart rate is above or below some predetermined level such as 60 heartbeats per minute. This indication, in turn, can be used by the patient as a self-diagnostic tool for injecting appropriate drugs to combat heart attack symptoms. Alternatively, it can be used in conjunction with a central diagnostic office to confirm instructions that are given over the telephone for self-administered drugs, etc.

However, if the subject's actual heart rate is very close to the crossover point (e.g. 60 beats per minute) it is conceivable that the two logic lights might oscillate or fluctuate in some undeterminable manner unless special precautions are taken. This is all the more so because of aberrations in the normal heartbeat pattern that are to be expected in much of the population.

Accordingly, the exemplary embodiment described below includes circuitry to prevent a logic light output from changing instantaneously. In particular, in the exemplary embodiment, the change from the high heart rate logic light to the low heart rate logic light is made only if two successive determinations of a low heart rate are detected. Similarly, if the low level logic light is energized, three successive determinations of a higher heart rate are required before the low rate logic light is extinguished and the high rate logic light is energized. As will be explained in more detail below, there are significant medical reasons for requiring such confirmation of changes in the heart rate before changing the output indications.

The exemplary embodiment includes a unique type of on-off switching arrangement which automatically turns the device on as soon as the user picks it up. Basically, this involves, in the exemplary embodiment, a conducting ground plate (which may be formed of a carbon loaded plastic material) on the backside of the case together with a plurality of separate conductive buttons or areas on the front side of the case respectively corresponding to the possible operational modes of the device. When the user just picks up the case, as in a normal holding position, his fingers will complete the electrical circuits from the back groundplate to one of the front conductive buttons thus selectively actuating the instrument in a particular desired operational mode. Very low current level logic circuits are utilized to detect the circuit thus completed by the user's hand so that when the instrument is not energized there is effectively almost no current drain on the battery. However, once these low current level logic circuits are changed in state (as by picking up the instrument), they turn on higher current level circuits actually utilized in the amplifiers, oscillators, output circuits, etc., of the device.

Besides considerable structural advantages for this particular arrangement of heart monitoring instrument, there is another very significant advantagement to such an arrangement. Since the device is entirely portable and unconnected to the usual grounding circuits, etc., for supressing 60 cycle hum or other ambient ac noise, there is no available source of ground potential for use in the usual third wire grounding circuit to suppress such noise. However, since the groundplate on the back of the exemplary embodiment is, in use, in electrical contact with the human body of the user, this will in itself constitute a significant source of ground reference potential which can be used to constitute an effective third wire ground reference for reducing 60 cycle or other ambient ac noise in conventional ground return noise rejection circuits.

The exemplary embodiment is of small size and light weight so that it may be portably carried on the body of the user at all times and conveniently held in his hand when in actual use. It is quite a small physical package. Nevertheless, a significant audio output level is required for alerting the user and/or other persons since the device may be utilized in high ambient audio noise conditions. Furthermore, a sufficiently high audio output level is required for driving the usual telephone transmitters without any special acoustical coupling, etc. The usual loudspeaker arrangement not only requires a heavy transformer and draws a lot of electrical current but is a rather bulky apparatus. Accordingly, the exemplary embodiment to be described below has achieved a significant improvement by enhancing the audio output from the usual direct coupled low-current conventional earphone through providing it with a special acoustic output coupling in the form of an elongated tubular structure having a predetermined length.

Since the exemplary embodiment is battery powered, a battery testing procedure is provided. However, it is not the usual type of battery testing procedure which involves placing a large load across the battery and observing the voltage drop that results to test the reserve capacity of the battery. Normally, this type of loading is used in battery testing procedures and, if the battery cannot sustain such a large load and still produce its rated output voltage, it is determined that the battery needs to be replaced.

However, since the exemplary embodiment must have a long shelf life and maximum battery replacement intervals, etc., the testing procedure must put as little strain on the battery as possible. This is all the more so since the device is to be carried upon and used by a person having greater than usual concern for his heart activity and for the readiness of the device. Accordingly, such a person might be expected to continually trigger the battery testing device out of an excessive precaution, etc., and, accordingly, the exemplary embodiment incorporates a very low current drain technique for testing the reserve battery capacity.

In essence, this technique involves a novel adaptation of otherwise normal circuitry included in the device to provide a regulated output voltage for the electronic amplifiers, oscillators and other circuits involved in the device. In conjunction with the voltage regulator, there is a normal safety circuit involving appropriate logic and voltage level comparison circuits whereby a reference voltage is effectively compared to the regulated output voltage and, if the regulated output voltage is not greater than the reference voltage, the whole circuitry is automatically shut down. In effect, the special technique involved is to raise the reference voltage temporarily during the testing cycle thus causing an automatic shut down of the unit if the voltage regulator fails to provide this temporary demand for an increased output voltage.

As can be appreciated, this special procedure does not put any substantial additional strain on the battery. Rather, it effectively only looks at the output of the voltage regulator and indicates when that output begins to drop to some level which is still above the minimum level that is usually permitted to exist for normal operation of the circuits. Thus, the user by testing the battery does not put any undue drain on the battery and always insures that there is, in fact, an appropriate "reserve tank" of energy in the battery.

Another unique and highly advantageous structural feature of the exemplary embodiment relates to the storage of the electrodes and attached wire leads. The physical configuration of the exemplary embodiment is such that the electrodes and their associated leads may be conveniently wrapped and stored right on the backside of the instrument. Furthermore, the electrodes are only frictionally lodged within an appropriate recess or open-faced storage compartment on the back of the instrument such that they may be easily shaken loose with one hand by the user. In addition, the permanently connected lead wires are stored by wrapping them about a wire-wrap structure disposed about the perimeter of the electrode storage compartment on the backside of the housing. Accordingly, both the wire leads and the electrodes can be conveniently wrapped about and snapped into the back side of the instrument thus providing a convenient and eye appealing storage capability, that is at the same time always ready for immediate access and use.

Other advantages and features of the exemplary embodiment both in terms of functional characteristics and/or capability and/or structural features will become more readily apparent from the following detailed description of the exemplary embodiment taken in conjunction with the drawings, of which:

FIG. 1 is a fron view of the control and output side of the housing of the exemplary embodiment;

FIG. 2 is a view of the opposite or backside of the housing for the exemplary embodiment showing the wires and electrodes in their normal storage positions and showing a battery compartment portion of the housing partially opened;

FIG. 3 is another view of the housing backside on which the electrode and wire storage features are disposed showing the lead wires and electrodes as they appear outside the storage areas and in condition for use;

Figure 6:
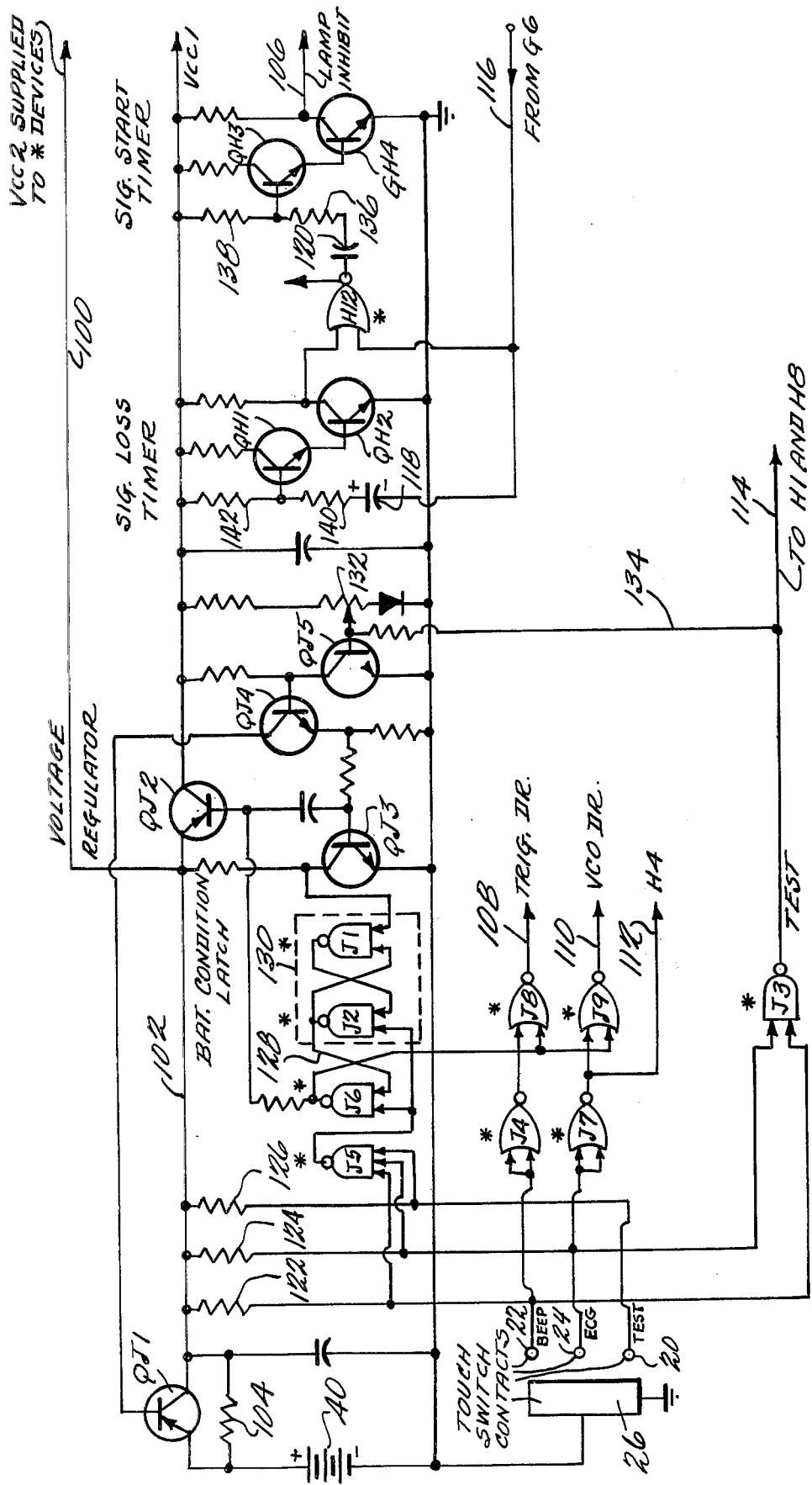
FIG. 6 is a schematic diagram of exemplary control and voltage regulator circuits for the exemplary embodiment.
Figure 7:
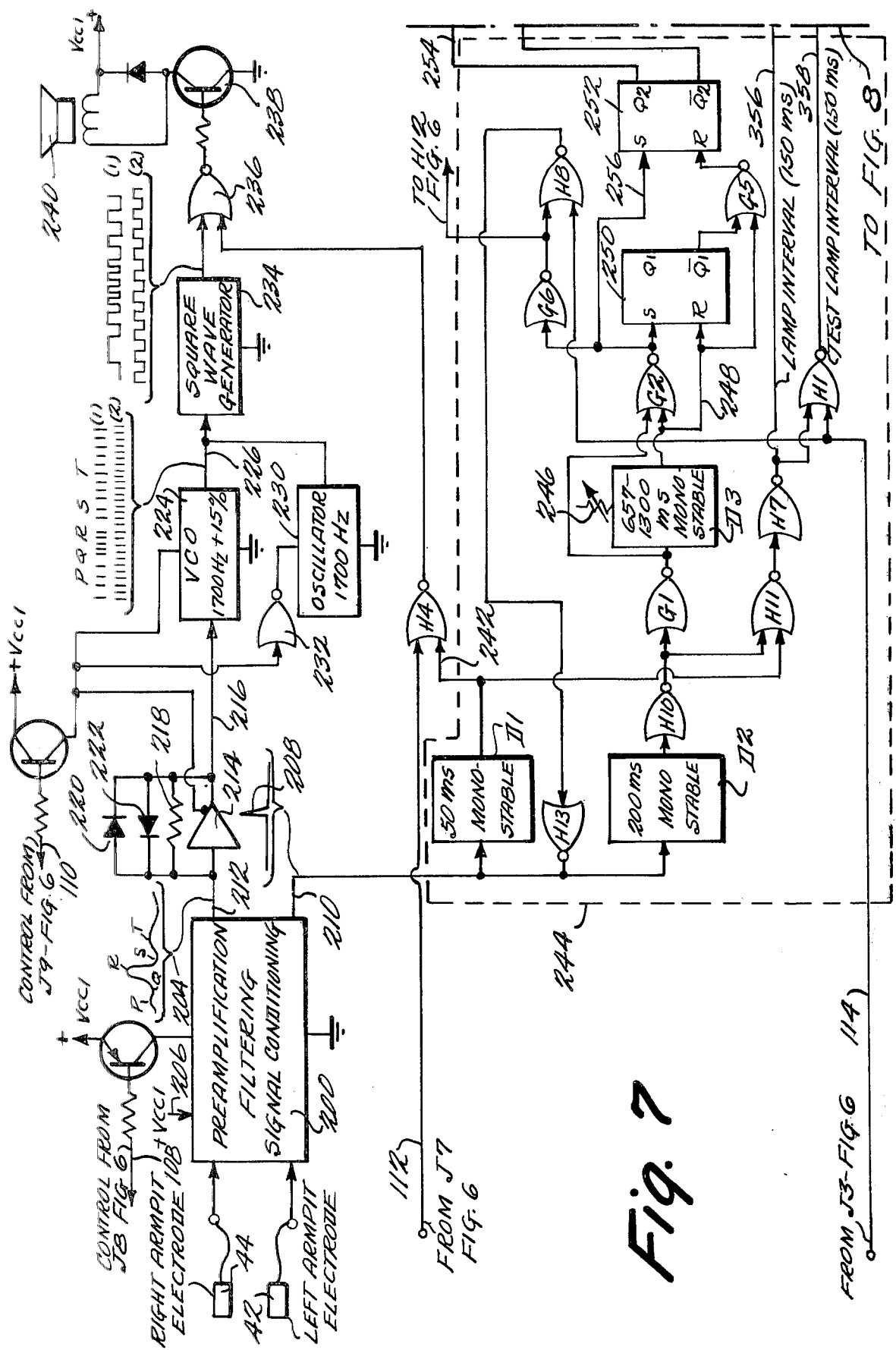
Figure 13:
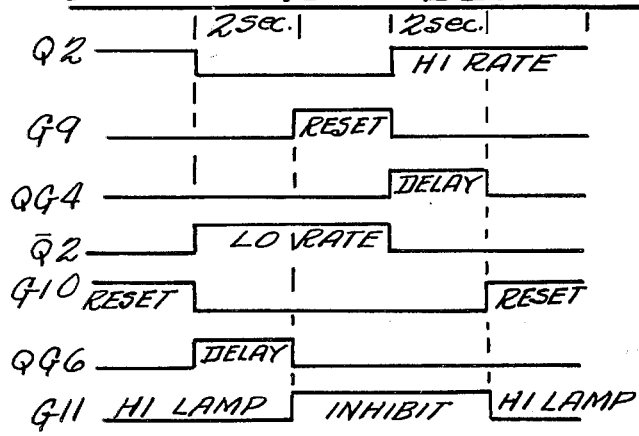
Figure 14:
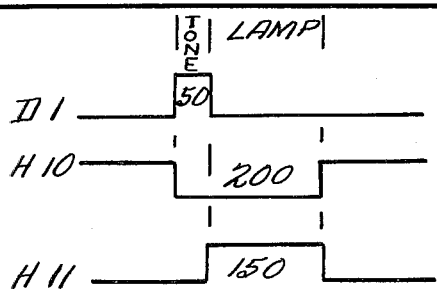
Figure 15:
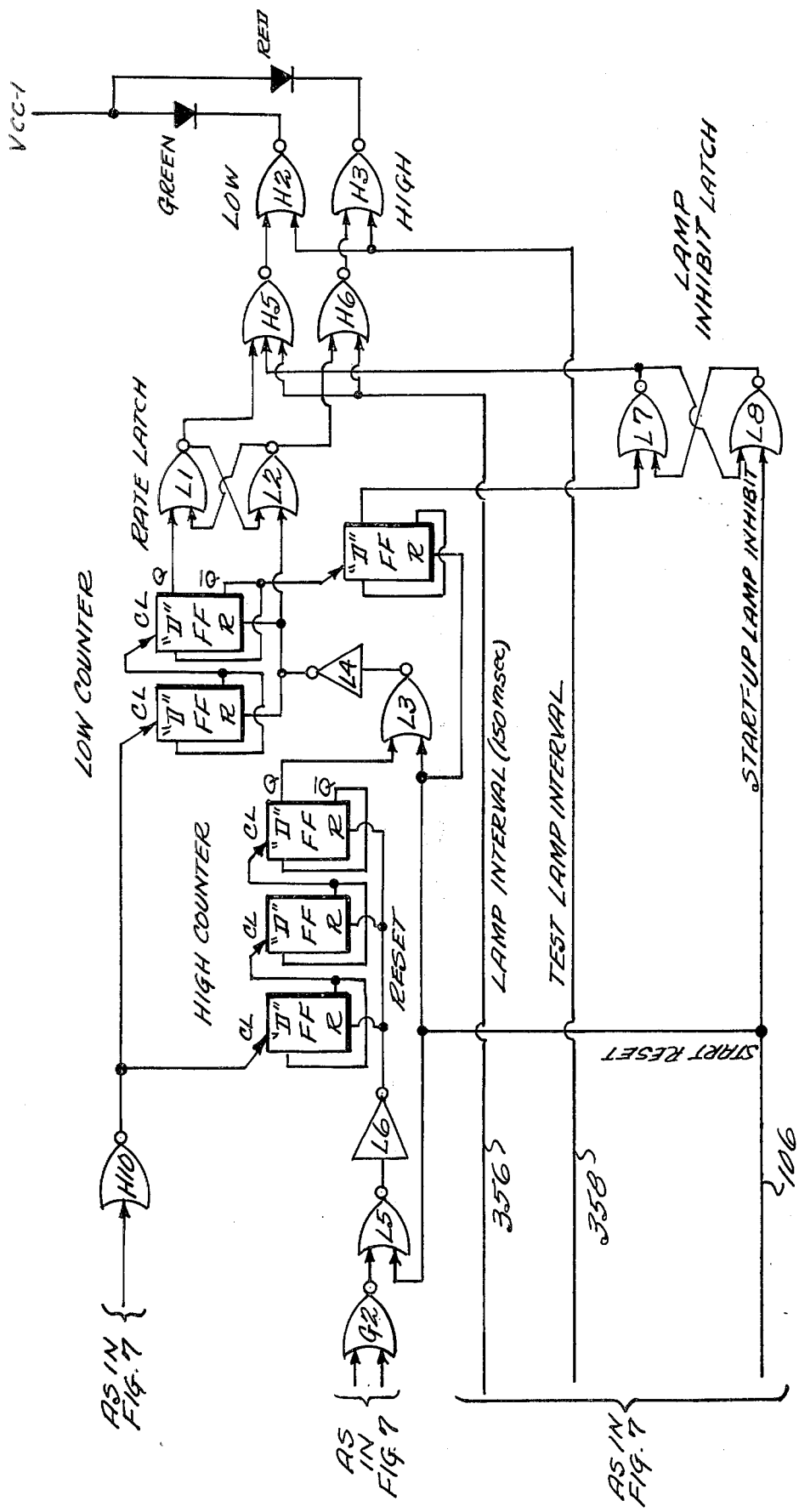

FIGS. 7 and 8 constitute a schematic diagram for electrical processing circuits of the exemplary embodiment;

FIGS. 9–14 are exemplary voltage level diagrams for various identified points in the exemplary circuits of FIGS. 6–8 for different operational modes of the exemplary embodiment, which voltage level diagrams are useful in explaining and understanding the operation of the circuits shown in FIGS. 6–8; and FIG. 15 is a schematic diagram of an alternate exemplary embodiment for a portion of the circuitry shown in FIGS. 7–8.

Figure 4:
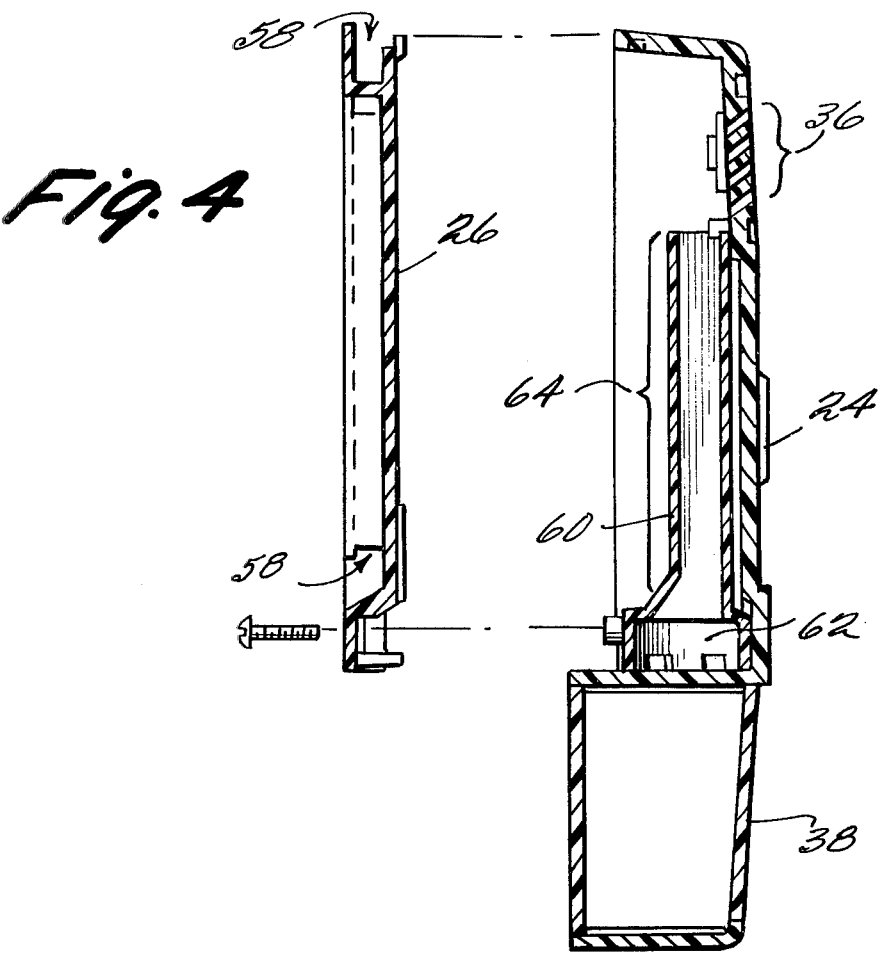
FIG. 4 is a vertical cross-section of the housing for the exemplary embodiment showing a special acoustic member therein for enhancing the audio output of the device.
Figure 5:
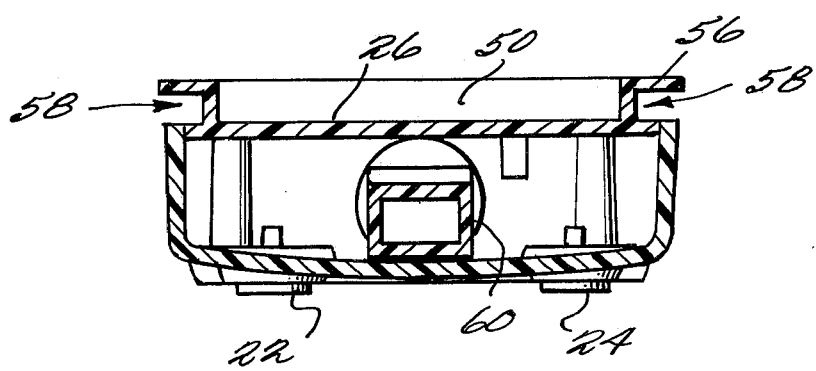
FIG. 5 is a horizontal cross-section of the housing for the exemplary embodiment also showing the special acoustic member shown in FIG. 4.

The structural features of the housing for the exemplary embodiment are shown in FIGS. 1–5 where FIGS. 1–3 are drawn approximately to scale, while FIGS. 4–5 are drawn approximately to one and one-half scale.

A frontal view of one side of the housing is shown in FIG. 1. For purposes of discussion, this particular side of the housing will be referred to as the "front" side although, it should be apparent that designation as the front or back side is merely one of definition. However, it is the side shown in FIG. 1 that will normally be facing the user when the instrument is in use. Thus, the user will normally pick up the instrument in his hand in such a manner that the four fingers of the hand are on the "back" side of the instrument while the thumb is on the front side of the instrument and can be selectively placed on conductive areas 20, 22 or 24 which are respectively labeled in FIG. 1 as TEST, BEEP and ECG. By so doing, the user will complete an electrical circuit, through his hand, between a groundplate 26 (shown in FIG. 3) and a selected one of the conductive areas 20, 22 and 24 thus selectively activating the instrument in a desired mode of operation.

Preferably, the entire body or housing is formed from conventional plastic materials by conventional forming processes. The conductive groundplate 26 may be formed by loading that portion of the plastic housing with carbon and/or by affixing a thin coating or layer of conductive material on this portion of the housing as should be apparent.

The front side of the housing is also provided with areas for providing sensible output indications related to the detected functioning of the heart. Accordingly, as shown in FIG. 1, medicament designating lights 28 and 30 are provided and are distinguished from each other by differently shaped surrounding areas 32, 34 respectively, which surrounding areas 32 and 34 may also be further distinguished by different color coding corresponding to similar color coding on two automatic injectors (now shown), for example, containing atropine and lidocaine that may be self-administered by the user depending upon which one of the logic lights 28 or 30 is activated and/or upon instructions received from a central diagnostic center.

A further output indication provided from the front side of the instrument as shown in FIG. 1 is an audio output which issues forth from an audio output port 36 which, in the exemplary embodiment, comprises a series of slots formed in the front side of the housing.

The bottom portion of the housing comprises a slidable portion 38 which opens as shown in FIG. 2 to permit access to a battery 40 for powering the electrical circuits of the device. As shown in FIG. 2, the back side of the instrument also includes storage provisions for the electrodes 42 and 44 as well as the lead wires 46, 48 respectively associated therewith. The electrodes 42 and 44 cooperate with an open-sided storage compartment 50 (above and/or a part of the groundplate 26 in the exemplary embodiment) into which the electrodes are frictionally inserted in a flat side-by-side relationship as shown, for instance, in FIG. 2. A depending tab 52 is provided to physically separate the top portion of the two electrodes and to help define a stable storage position for each of the electrodes 42 and 44 as should be apparent.

In the exemplary embodiment, the electrode leads 46 and 48 are permanently connected between the respectively associated electrodes 42 and 44 and a common exit port 54 (see FIG. 3) from the housing. Accordingly, an integrally formed wraparound storage structure 56 is provided about the outside perimeter of the storage compartment 52 on the back side of the housing for wrapping and storing lead wires 46 and 48 as shown in FIG. 2. As perhaps best seen in FIGS. 4 and 5, the wraparound storage structure 56 in the exemplary embodiment comprises an easily accessible peripheral slot 58 into which the lead wires can be wrapped.

Since, in the exemplary embodiment, the electrodes 42 and 44 are stored in a flat side-by-side relationship (as shown in FIG. 2), and since the permanently connected lead wires issue forth from a common exit port 54, the lead wires 46 and 48 in the exemplary embodiment have been dimensioned so as to have lengths which differ by essentially the width of one of the electrodes. That is, as seen in FIG. 2, the points at which the leads 46 and 48 respectively connect to their electrodes 42 and 44 are physically separated by a horizontal distance that is approximately equal to the width of one electrode since the leads, as shown in FIG. 2, are approximately connected to the middle of each electrode member. Accordingly, lead 46 connected to electrode 42 is made just this much longer than lead 48 (as is shown approximately in FIG. 3) so that when the lead wires are wrapped about the storage structure 56 and the electrodes are stored within their storage compartments, there is no excess lead wire as should now be appreciated.

Another significant feature of the exemplary embodiment shown in FIGS. 4 and 5 is the acoustic enhancement means 60. A conventional relatively low power audio output means such as an earphone which can be directly coupled to an electronic amplifier without the need for a transformer or the like is placed within a lower portion 62 such that the audio output is provided at the top side thereof or at the bottom end of an elongated tubular structure 64 having a predetermined length for acoustically coupling and enhancing the audio output from the earphone or the like so that the audio output provided from the top end of the elongated tubular structure 64 and through the audio output port 36 is sufficient to drive the conventional telephone transmitter and/or to be heard above ambient noise levels to be commonly expected. The length of the elongated tubular structure in 64 in the exemplary embodiment is approximately 1 11/16ths of an inch in length which has been found preferable for a median operating frequency of approximately 1700 Hertz. As should be apparent, different lengths for the elongated tubular structure 64 would be preferable for other median operating frequencies.

A schematic diagram of electrical circuits for the exemplary embodiment is shown in FIGS. 6–8. In general, FIG. 6 comprises control circuits while FIGS. 7 and 8 comprise processing and output circuits for receiving and processing electrical signals taken from a human body representing the functioning of a heart beating therewithin and for providing sensible output indications corresponding to a predetermined one or more characteristics of the electrical signals. Control signals developed in the circuits of FIG. 6 are utilized in the circuits of FIGS. 7-8 to achieve desired operating modes that will be discussed in more detail below. Furthermore, voltage level diagrams for various modes of operation are shown in FIGS. 9-14 and are quite helpful in understanding the operation of these exemplary electrical circuits. For instance, the voltage level diagrams of FIGS. 9-11 generally relate to the operation of circuits shown in FIG. 6 while the voltage level diagrams shown in FIGS. 12-14 generally relate to the operation of circuits shown in FIGS. 7-8.

As should be apparent from the drawings, FIGS. 7 and 8 should actually be placed together and considered as one circuit diagram and the circuits shown therein will be discussed hereafter accordingly.

While the exemplary electrical circuits discussed below are shown as discrete component circuits, those in the art will recognize that it is preferable to actually realize such circuits or their equivalents with conventionally designed integrated circuit techniques thus permitting the described electronic functions to be achieved in the smallest possible physical space.

As shown in FIG. 6, there are essentially 7 outputs from the control circuits shown in the exemplary embodiment. The supply voltages Vcc2 and Vcc1 are provided to power all of the electrical circuits. Supply voltage Vcc1 is a regulated output voltage supplied to power the relatively higher power amplifiers, oscillators, flip-flops, drivers, etc. It is only supplied when the unit is activated in one of its three operational modes, namely, the BEEP mode, the ECG mode and/or the TEST mode. On the other hand, the supply voltage Vcc2 is directly connected via line 100, line 102 and resistor 104 to the positive terminal of battery 40 and is thus supplied at all times regardless of whether the unit is activated or not. It is supplied only to those devices that are marked with asterisks in the drawings, which devices are special very low current devices (e.g. COSMOS circuits) which typically draw less than a microamp of current altogether. Accordingly, no really significant current is drawn from the battery 40 in its stand-by or inactivated state. It is only when these very low current level devices are triggered into one of the three modes of operation that the higher powered devices are activated and the supply voltage Vcc1 is provided.

The control outputs on lines 106, 108, 110, 112 and 114 are supplied to the circuits of FIGS. 7-8 and their effects will be discussed with respect to the circuitry of that figure. However, the generation of these control signals will now be discussed with respect to the circuit of FIG. 6. Also, as shown in FIG. 6, there is a signal supplied on line 116 from the circuit of FIGS. 7-8 to the circuit of FIG. 6.

The voltage levels depicted in FIGS. 9-11 at the output of various elements shown in FIG. 6 have been shown as simply low and high relative levels. As will be appreciated by those in the art, these levels might be of different sign and/or, one of the levels might be a reference potential such as ground. For ease of discussion in the remainder of this description, the high voltage level will be referenced as + while the low voltage level will be referred to as −.

In the quiescent or non activated mode (labeled off in FIGS. 9-11) the Vcc2 power is supplied to the elements having an asterisk in FIG. 6 and, it will be seen that both of the inputs to NOR gates J4 and J7 are + thus making their outputs − and providing a − control voltage on line 112. Furthermore, all of the inputs to NAND gate J5 will be + thus making its output − and, since its output is connected to one input of the NAND gate J6, the output of gate J6 will be +. Since this + input is supplied to both of the NOR gates J8, J9, the control outputs on lines 108 and 110 will both be − in the quiescent mode.

Similarly, both inputs to the NAND gate J3 will be + thus making its output − for the control signal provided on line 114 in the off mode. Since the output of NOR gate G6 (to be discussed with respect to FIGS. 7-8) is also − in the quiescent mode, the capacitor 118 will eventually charge as shown in FIG. 6 to cause transistors QH1 and QH2 to take on their conducting or saturation state, thus, effectively grounding the collector of transistor QH2 and providing another − input to the NOR gate H12. Accordingly, since the NOR gate H12 has two − inputs, its output will be + in the off or quiescent mode. Similarly, once capacitor 120 becomes charged transistors QH3 and QH4 will be in their conducting state thus effectively grounding the collector of QH4 on line 106 and providing a − control signal on this line as well.

When the operator's or user's hand bridges the ground plane 26 with any one of the conductive buttons 20, 22 or 24, resistors 122, 124 and 126 are sized (with respect to the maximum expected skin resistance between the plate 26 and buttons 20, 24 and 22, e.g., two megohms), such that at least one of the inputs to the NAND gate J5 will go − thus causing the output of J5 to go + no matter which one of the activated modes is involved. When this occurs, the NAND gate J6 may take on a different state than previously if the output on line 128 from the battery condition latch 130 is +. That is, if the output of the battery condition latch is still + (indicating that a sufficient battery capacity is available), then the output of J6 will change whenever any one of the activated modes is indicated by the change in output from NAND gate J5 thus providing a − output from NAND gate J6 which, in turn, is presented as a − input to the NOR gates J8, J9. Thus, unless the normally negative outputs from NOR gates J4 and J7 are changed, the output from NOR gates J8 and J9 on lines 108 and 110 will be changed from − to +.

Since, in the TEST mode, no change is made to the input of NOR gates J4 and J7 it follows that in the TEST mode the output on lines 108 and 110 goes positive.

However, in the BEEP mode it can be seen that the inputs to NOR gate J4 will be changed from + to − thus causing one of the inputs to NOR gate J8 to be + and inhibiting any change in the output of J8 such that the control signal on line 108 would remain negative in the BEEP mode. Of course, since in the BEEP mode no change is made in the inputs to NOR gate J7, the output on line 110 will switch from − to + in this mode of operation.

Similarly, when the ECG mode of operation is selected, the inputs to NOR gate J7 will go − thus causing its output to go + and inhibiting any change in the output of gate J9 thus causing the control signal on line 110 to remain − while the control signal on line 108 is permitted to change to +.

Since both inputs to the NAND gate J3 are connected to buttons 22 and 24 respectively, activation of the unit in anything other than the TEST mode will cause at least one of the inputs to go − thus causing the output from J3 to change from − to + when the unit is activated except in the TEST mode where it remains − because neither of the inputs to the NAND gate J3 are affected in this mode of operation.

Accordingly, it can be seen that when the unit is activated to any of its three possible operational modes, the output from NAND gate J6 goes − thus turning on transistor QJ2 and activating the voltage regulator which will supply the voltage Vcc1 to the rest of the circuitry. Of course, if the output on line 128 from the battery condition latch 130 ever goes −, the NAND gate J6 will be inhibited from changing its output thus preventing the transistor QJ2 from ever turning on or conducting and thus preventing the supply voltage Vcc1 from ever being supplied to the remainder of the circuitry.

The magnitude of the regulated output voltage Vcc1 is controlled by the preset potentiometer 132 which adjusts the bias voltage supplied to the base of transistor QJ5 thus controlling the collector voltage of that transistor which, in turn, controls the base current for transistor QJ4 which, in turn, controls the base current for the actual regulator transistor QJ1 which varies its effective conductivity as necessary to maintain regulated output voltage selected by the positioning of potentiometer 132.

In addition, transistor QJ3 is employed, effectively, as a voltage level detector which is connected to saturate or conduct whenever the voltage regulator transistors QJ5, QJ4 and QJ1 are unable to maintain the desired magnitude of regulated output voltage Vcc1 as determined by the base current for transistor QJ5. Whenever this insufficient battery capacity condition is indicated, transistor QJ3 conducts thus presenting a − input to the NAND gate J1 forming part of the battery condition latch 130. This negative input causes the output of J1 to change from − to + which, in turn, causes the output from NAND gate J2 on line 128 to change from + to − thus inhibiting any change in the output of gate J6 such that the transistor QJ2 can never be turned on to activate the voltage regulator and supply Vcc1 for the other circuitry. As can be seen, each time an attempt is made to activate the unit, the output of NAND gate J5 is utilized to reset battery condition latch 130.

The just described actuation and operation of the voltage regulator, etc., will occur as described whenever the unit is activated in either the ECG or BEEP modes and the signal on line 114 from the output of NAND gate J3 is + (as previously described) thus supplying an appropriate additional bias to the base of transistor QJ5, which, in addition to the setting of the potentiometer 132, determines the magnitude of voltage Vcc1 that is demanded by the voltage regulator circuitry. However, when the unit is activated in the TEST mode, the output from NAND gate J3 remains − thus preventing any extra bias current along line 134 to the base of transistor QJ5 and, in effect, this provides a temporary demand for an increased level of regulated output voltage Vcc1. As should now be appreciated, if this temporarily increased demand is not met, transistor QJ3 will conduct and set the battery condition latch 130 thus inhibiting the output of gate J6 and preventing the transistor QJ2 from turning on.

Normally, when the unit is activated, the voltage level on line 116 from NOR gate G6 (see FIGS. 7–8) has a relatively high duty cycle of positive excursions (see FIG. 11). Accordingly, as will be appreciated from FIG. 6, the output of NOR gate H12 will be substantially maintained at a negative level and, until capacitor 120 discharges through resistors 136 and 138, transistors QH3 and QH4 will be turned to their non-conducting or off state thus providing a positive lamp inhibit signal on line 106 for a time duration determined by the discharge time constants of the resistance-capacitance circuit defined by capacitors 120 and resistors 136, 138 as should now be apparent.

Furthermore, during operation, capacitor 118 will be charged opposite to the polarity shown in FIG. 6 thus readying the signal loss timer circuit comprising transistors QH1 and QH2 for operation. Accordingly, transistors QH1 and QH2 will be turned off for a time period determined by the RC time constant of capacitor 118 in combination with resistors 140 and 142. After this time period has passed, the other input to NOR gate H12 in FIG. 6 will also be − thus causing the output of NOR gate H12 to be + and charging capacitor 120 as in the quiescent state so that the signal start timer is again ready to provide the lamp inhibit signal 106 as soon as the high duty cycle + signals on line 116 reappear thus inhibiting spurious responses even after the initial start-up or activation of the unit if the signal should be temporarily lost and then reappear.

The signal input to the electrical circuits originates at the left and right armpit electrodes 42 and 44 as shown in FIG. 7. These signals are input to conventional preamplification, filtering and signal conditioning circuits 200 which, inter alia, include differential amplifiers providing common mode rejection of AC signals such as 60 Hertz noise when used in combination with a ground reference potential provided by the contact plate 26 in contact with the user's body. The conventional amplification, and filtering circuits which provide a replica of the usual heartbeat signal 204 (e.g. the usual PQRST waveform pattern shown in FIG. 7) are supplied with power directly from Vcc1 on line 206 in the exemplary embodiment while other signal conditioning circuits which provide a single spike or pulse 208 on line 210 in response to each detected R portion of the heartbeat waveform are supplied with power Vcc1 through a transistor switch 202 which is controlled by the trigger drive on line 108 from NOR gate J8 in FIG. 6. Accordingly, whenever the control from NOR gate J8 is − and the regulated voltage Vcc1 is available, (ie., the BEEP mode) the switch transistor 202 will supply the signal conditioning circuits with voltage so that the spike waveforms 208 corresponding to each detected heartbeat will be provided on line 210.

Accordingly, the PQRST analogue waveform 204 will be provided on line 212 in either the BEEP or ECG mode while the trigger pulses 208 corresponding to each detected heartbeat will appear on line 210 only in the BEEP mode.

The amplifier 214 has its input connected to receive the analoque PQRST signal thus controlling the magnitude of a similar analogue signal at its output on line 216 as determined by its gain which is controlled by the feedback resistor 218 and limited on both directions by the parallel connected back-to-back diodes 220 and 222 as will be appreciated by those in the art. The purpose of limiting the magnitude of the output signal on line 216 will soon become apparent.

As shown in FIG. 7, the analogue output from amplifier 214 is applied to control the frequency of a conventional voltage controlled oscillator 224 which has a nominal or center frequency of 1700 Hertz and which is varied in frequency plus or minus 15% depending upon the input signal on line 216. Accordingly, the output on line 226 will appear as waveform (1) shown above that portion of the diagram as a series of narrow pulses having an instantaneous frequency proportional to the instantaneous magnitude of the PQRST waveform.

As shown in FIG. 7, the amplifier 214 and voltage controlled oscillator 224 are both supplied with power Vccl via a switching transistor 228 which is turned on whenever the output from NOR gate J9 (see FIG. 6) is − and the regulated supply voltage Vccl is supplied. As previously described, this condition occurs when the unit has been activated in the ECG mode.

A constant frequency oscillator (center frequency of 1700 Hertz) 230 is fed with supply voltage from an inverter 232 connected to the switched Vccl supply from transistor 228. Accordingly, whenever the Vccl voltage is being supplied to amplifier 214 and the voltage controlled oscillator 224, the constant frequency oscillator 230 is not supplied with voltage and is thus inoperative. Conversely, when the amplifier 214 and voltage controlled oscillator 224 are not being supplied with voltage via transistor 228, the constant frequency oscillator 230 is supplied with power and is thus operative to produce constant frequency pulses at 1700 Hertz as shown at waveform 2 above this portion of the drawing in FIG. 7.

Whether the pulses on line 226 are of the variable frequency type 1 or constant frequency type 2, they are input to a squarewave generator 234 (e.g., a toggle or flip-flop connected to change state each time it is triggered) to produce corresponding waveforms as shown in FIG. 7. The output from the squarewave generator 234 is then fed through a NOR gate 236 onto an audio driver stage 238 which drives a conventional direct coupled earphone audio output device 240.

In the ECG mode, the control signal on line 112 (see FIG. 6) from NOR gate J7 is + thus causing the NOR gate H4 (see FIG. 7) to have a − output. Accordingly, the lower input to the NOR gate 236 shown in FIG. 7 is − in the ECG mode thus causing the gate 236 to be triggered at the variable frequency rate as indicated by waveform 1 in FIG. 7 and producing a variable frequency output from the audio device 240 having an instantaneous frequency related to the magnitude of the PQRST waveform as should now be apparent.

In the BEEP mode, the signal from NOR gate J7 is − thus causing gate H4 to have a + output except when its input on line 242 from a 50 millisecond monostable D1 goes positive. Accordingly, the NOR gate 236 is switched at the 1700 Hertz rate by waveform 2 only during the 50 millisecond time period when the monostable D1 causes the output from NOR gate H4 to go −. As also shown in FIG. 7, the 50 millisecond monostable D1 is triggered from the spikes 208 on line 210 once for each detected heartbeat so that, in effect, when the unit operates in the BEEP mode a 50 millisecond burst of 1700 Hertz audio energy is emitted from the audio output device to 40 for each detected heartbeat.

As those in the art will appreciate, audio tones of approximately 2500 Hertz should not be transmitted over conventional telephone circuits since they cause switching functions to occur. Accordingly, the gain of amplifier 214 is so limited by diodes 220, 222 as to prevent the control voltage to VCO 224 from ever producing oscillations of such frequency.

Figure 12:
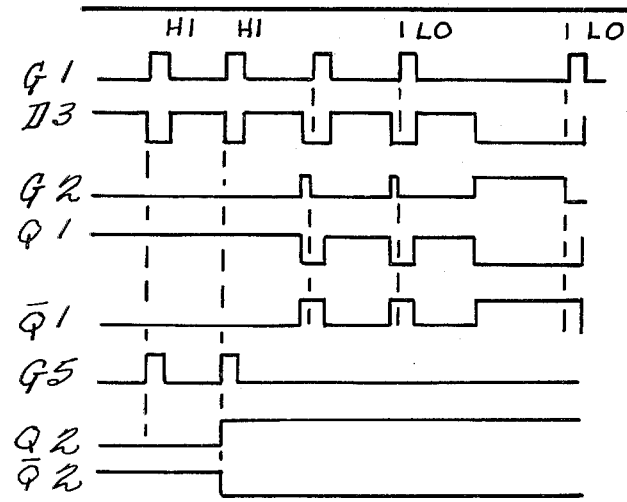

Although some of the voltage level diagrams in FIGS. 12–14 have been implicitly referenced heretofore, it will be increasingly helpful to refer to these figures during the following discussion of the rate detecting circuitry generally shown within dotted lines 244 in FIG. 7.

As previously discussed, the spikes 208 on line 210 trigger the 50 millisecond monostable D1. In addition, these spikes also trigger a 200 millisecond monostable D2 whose output is inverted by NOR gate H10 to provide an inverted input to NOR gate H11 before being again inverted by NOR gate G1 to trigger another monostable D3 whose period is variable depending upon the adjustment of preset parameters such as potentiometer 246 within a range of approximately 657 to 1300 milliseconds. D3 is a monostable which is triggered by negative going transitions such that, for each detected heartbeat, there will be a positive going 200 millisecond pulse at the output of G1 followed by a positive going pulse at the output of monostable D3 having a duration determined by a preset parameter such as potentiometer 246. As will be seen, the setting of potentiometer 246 or selection of the delay for the monostable D3 effectively determines the cross-over point or rate for deciding whether a given heart rate is high or low. Typically, the rate may be set at a value such as 60 beats per minute by setting delay D3 to equal 800 MS so that the total delay of D2 + D3 equals the period between 60 beats per minute pulses.

So long as the heartbeats occur at a sufficiently rapid rate, one or the other of the inputs to NOR gate G2 will always be + thus keeping its output − as may be seen, for example in FIG. 12. At the same time, since pulses are appearing on line 248 (the output of monostable D3) the flip-flop 250 will have been reset such that its output $Q_1$ goes + as shown in FIG. 12. Of course the output $\overline{Q}_1$ would also be − or just the opposite of $Q_1$ as should be apparent. Accordingly, one of the inputs to NOR gate $G_5$ will be constantly − when a high pulse rate is being processed while the other input will be switching from + to − with the output from the monostable D3 as should be apparent. Accordingly, the output of gate G5 will also vary between − and + levels to insure that flip-flop 252 has been similarly reset to provide a positive signal Q2 on line 254 indicating that a high pulse rate has been detected.

On the other hand, if a low pulse rate is being received, the interval between pulses or triggers 208 on line 210 will be such that both the 200 millisecond monostable D2 and the preset monostable D3 will have timed out thus causing both of the inputs to NOR gate G2 to go − and thus causing the output of gate G2 to change between − and + levels as shown in FIG. 12. As should now be apparent, this transitioning at the output of gate G2 will result in the setting of flip-flop 250 and cause the signal $\overline{Q}1$ to vary between + and − values as also shown in FIG. 12. Since one of the other of the inputs to gate G5 is now always +, its output will remain at a − level and thus flip-flop 252 will not be continually reset as was the case when a high pulse rate was being detected as previously discussed.

At the same time, the now variable output level from the gate G2 is applied via line 256 to the set input terminal of flip-flop 252 such that the output $\overline{Q}2$ now goes + and Q2 goes − thus providing a + voltage on line 258 indicating a low pulse rate occurrence.

As will be seen, the output from NOR gate G2 changes only when low pulse rates are detected and, since that output is presented through NOR gate G6 to control the previously discussed gate H12 in FIG. 6, it will be seen that the signal on line 116 is constantly + when a high rate is being detected and has a very high duty cycle of + voltage level even during the low pulse rates unless the signal is lost altogether which, of course, serves as a sign that the signal has been lost as previously discussed with respect to the signal loss timer and signal start timer in FIG. 6.

In addition, during the TEST mode of operation, the voltage from NAND gate J3 (FIG. 6) goes − and, since this is provided as one of the inputs to NOR gate H8 in FIG. 7, it may be seen that gate H8 is enabled during the TEST mode of operation to change its output state from − to + in response to changes of + to − from the output of gate 6. Thus, in the TEST mode, when the signal on line 114 goes −, the output of gate H8 will go + and, after inversion by the NOR gate H13, will trigger monostables D1 and D2. The output of monostable D1 will then proceed to gate a 50 MS burst of 1700 Hertz audio output through gate 236 as previously described while the monostable D2 will initiate a timing operation that will have to result in a determination of a low pulse rate since there is no following pulse on line 210.

However, as soon as the low pulse rate is detected, gates G2, G6, H8 and H13 will again change state thus triggering the same operation to repeat itself. Accordingly, as should now be apparent, the rate detection circuitry will be caused to effectively oscillate at a frequency exactly corresponding to the cross-over point (e.g. 60 beats per minute in the exemplary embodiment).

As already discussed, this will automatically test out the operation of the constant frequency oscillator, square-wave generator, gate 236 and audio output circuitry. In addition, as will become more apparent below, this testing procedure will also test the visual output related circuitry to insure that it is working properly and will, of course, permit one to externally observe or time the cross-over rate thus insuring that the monostable D3 has been properly adjusted. If out of adjustment, the rate being observed can be adjusted by adjusting the monostable D3 via means such as the potentiometer 246 until the desired cross-over rate has been achieved.

As should now be appreciated, the trigger signals 208 on line 210 are processed by the rate detecting circuitry 244 to result in a + signal on line 254 if the rate of heart-beats is in excess of a predetermined value and to produce a + voltage on line 258 if the detected rate is below that predetermined value. The circuitry shown in FIG. 8 then further operates upon these signals to insure that a spurious or premature change high-to-low or vice versa is not inadvertently permitted.

A low to high change inhibit means 300 and a high to low change inhibit 302 are provided to insure that at least some predetermined number of successive high pulse rate detections or low pulse rate detections respectively are detected before the visual output signals are changed from high-to-low or from low-to-high respectively.

There are important medical reasons underlying the choice of different predetermined numbers for these inhibited rate change indications in the exemplary embodiment. For instance, assume that the heartbeat being monitored is approximately at the cross-over rate, e.g., 60 beats per minute. There are many hearts which produce ectopic beats which normally come slightly earlier than would be expected followed by a relatively longer pause to put the next beat at its regularly expected location in time. As will be appreciated, this slightly misplaced ectopic heartbeat will result in two successive time intervals that are respectively shorter and longer than the interval to be expected for the normal 60 beat per minute rate. Accordingly, the circuitry would first detect a high heart rate while measuring the first time interval and then immediately thereafter detect a low heart rate when examining the second time interval. Actually, the average heart rate is still approximately 60 beats per minute (i.e., slightly below 60 beats per minute which should produce a constant low rate output indication or slightly above 60 beats per minute which should produce a constant high rate output indication) and the output indications should not be changed merely because a single ectopic heartbeat has occurred. Medically, the occurrence of a single ectopic heartbeat is not significant for the purposes contemplated by this monitoring device. Accordingly, both of the circuits 300 and 302 should be adjusted to insure that at least two successive determinations of a change in the heart rate are required before the output indication is actually changed. In effect, this would ignore the single ectopic heartbeat.

On the other hand, if three ectopic beats occur in succession, this is medically defined as ventricular tachycardia and calls for an injection of the drug lidocaine. This, in fact, is important information so that if an average low heart rate is being detected the output indication should, in fact, be changed from a low to a high indication if three ectopic beats are detected in succession. Accordingly, the circuit which controls a change of output indication from a low-to-high indication should be adjusted to provide such a change whenever three successive high rate determinations are detected.

In effect, the circuits 300 and 302 in the exemplary embodiment shown in FIG. 8 are analogue time delay circuits having time constants with respect to a nominal cross-over rate (e.g., 60 beats per minute) that would require three successive determinations of a high heart rate before changing the output indication from low-to-high and two successive determinations of a low heart rate indication before changing the output from a high - to - low indication. As will be shown below in the discussion of FIG. 15, digital counting circuitry can also be used to inhibit unwarranted changes in high/low output indications.

To explain the operation of the circuit shown in FIG. 8, first assume that the device is operating and detecting a high heart rate so that there is a + signal on line 254 and a − signal on line 258. In the quiescent state, all the transistors QG3, QG4, QG5 and QG6 would be in the conducting state so that there would be a − level input on the lower input of gate G9 in FIG. 8. Similarly, since both of the inputs to gate G10 are −, there would be a + output from gate G10 applied to one of the inputs of gate G11 which, in turn, would thus necessarily have a − output level. Now, assume that the detected rate has changed from this high value to a low value such that the + signal now appears on line 258 rather than line 254. It should be noted, that because of the pre-existing quiescent state, capacitor 304 is charged with a + voltage on the terminal connected to resistor 306 while capacitor 310 would be in a substantially uncharged state.

Accordingly, when the output of NOR gate G10 transitions negatively in response to receipt of a + voltage level on line 258, the transistors QG5 and QG6 will be temporarily turned off for a time duration determined by the time constant of the capacitor 310 and resistors 312, 314 as should be apparent. Thus, for a temporary time period, a + voltage level signal will be presented to the lower input of NOR gate G9 in FIG. 8, insuring that the output of gate G9 remains − and that capacitor 304 remains charged as previously stated. Furthermore, since this temporary + voltage level is also connected to the lower input of gate G11, its output will be maintained in a − state just as previously existed when a high heart rate was being detected. Accordingly, as should now be apparent, there will be no change in the output indications for the time duration of the delay afforded by circuit 302.

If the low heart rate is still being detected after the time delay of circuit 302, then the output from transistor QG6 will again transition − thus causing gate G11 to change its output from − to + which, as will be seen, will cause a change from a high output indication to a low output indication. At the same time, since both of the inputs to NOR gate G9 are now −, its output will go + thus permitting the capacitor 302 to substantially discharge. Of course, since the output of NOR gate G10 is now −, capacitor 310 will charge in a manner similar to that previously described for capacitor 304.

Now, if the detected heart rate changes back from low-to-high a similar train of events will occur when the level on line 254 goes + and the level on line 258 goes −. Here, the output of NOR gate G9 will go − thus temporarily turning off transistors QG3 and QG4 for a time period determined by the discharge characteristics of capacitor 304 and resistors 306, 308. Since transistor QG4 is temporarily turned off, a + input will temporarily be presented to gate G10 even though it has been removed from line 258 thus maintaining both of the inputs to gate G11 − and insuring that the + output from gate G11 remain temporarily at its preexisting level for the time duration of the delay caused by circuit 300. When circuit 300 does time out (and assuming that the new high heart rate detection is still present as indicated by a + voltage on line 254 and a − voltage on line 258), then when transistor QG4 turns on at the end of this time duration, gate G10 will have two − inputs thus causing its output to transition to + and, in turn, causing the output of gate G11 to go − again thus changing the output indication from low to high.

In the exemplary embodiment where a nominal crossover rate of 60 beats per minute is utilized, the low-to-high change inhibit circuit 300 should be adjusted to provide a delay of slightly more than one second while the high-to-low change inhibit circuit 302 should be adjusted to provide a time delay of slightly in excess of two seconds. Since one time interval will have already been measured before a change is ever indicated on lines 254 and 258, it should now be appreciated that these further time delays will produce the required count of two successive determinations of low heart rate before changing the output from a high indication to a low indication and three successive counts of a high rate determination when changing in the other direction.

As previously discussed, the output from gate G11 will be − when a high heart rate output indication is desired and + when a low heart rate output indication is desired. Accordingly, a − voltage level will be present at the middle input of NOR gate 350 whenever a high heart rate indication output is desired and, (because of NOR gate 352 operating as an inverter) a − voltage level will also be present at the middle input of NOR gate 354 whenever a low heart rate output indication is desired.

Temporary reference to FIG. 7 should now be made for understanding the derivation of the lamp interval signals on line 356 and the test lamp interval signals on line 358. Reference can also be made to FIG. 14 for an understanding of the generation of these signals.

As can be seen, each detected heart beat will produce a trigger pulse 208 which will, in turn, trigger a 50 millisecond output from monostable D1 appearing on line 242 which is, in turn, connected as one input to the NOR gate H11. Another input to the NOR gate H11 is the inverted output of the 200 millisecond monostable D2 which is triggered simultaneously with the 50 millisecond monostable D1. Accordingly, the output of gate H11 will be a positive going pulse of 150 millisecond duration for each detected heartbeat. After inversion by the NOR gate H7, this would be a negative going pulse of 150 milliseconds appearing on line 356 (FIG. 8) to provide an enabling − lower input to each of the NOR gates 350 and 354 previously discussed. Since the upper input to these NOR gates 350, 354 is connected to the lamp inhibit signal on line 106 from FIG. 6, which is normally −, this means that one of the gates 350, 354 will be fully enabled to change its output from − to + depending upon which one receives a − input from gate G11 or gate 352 respectively. That is, if a high heart rate is being detected, gate 350 will be fully enabled for 150 milliseconds after each detected heartbeat to change its output from − to +. On the other hand, if a low heart rate is being detected, only NOR gate 354 will be fully enabled during this 150 millisecond time interval. As will be explained below, the lower enabled inputs to gates 360 and 362 is normally − so that the output of both of these gates is normally + thus preventing either of the LED's (Light Emitting Diodes) 364, 366 from conducting. However, if a high heart rate is detected, then, for the 150 milliseconds that the output from gate 350 transitions from − to +, the output from NOR gate 360 will transition negatively thus causing the LED 364 to conduct for 150 milliseconds during each heartbeat while the detected heartbeat rate is high or above the predetermined changeover frequency.

Similarly, the NOR gate 362 output is transitioned from + to − for 150 milliseconds each heartbeat when the heart rate is below the predetermined level thus causing LED's 366 to emit light. Of course, the LED's 364 and 366 are mounted so as to provide visual outputs 28 and 34 as previously discussed with respect to FIG. 1.

Referring back to FIG. 8, it will be recalled that the control signal on line 114 is − during the TEST mode of operation but + during the BEEP or ECG mode of operation. Accordingly, during the BEEP or ECG modes of operation, the output of gate H1 will be forced to a − level thus providing the normal quiescent − level on line 358 enabling the gates 360 and 362 previously discussed with respect to FIG. 8. However, in the TEST mode, when the control signal on line 114 goes −, the output from gate H1 will be the inverted output of gate H7 or, in other words, the same as the output from gate H11 which is a 150 millisecond positive going pulse for each detected heartbeat. As will be appreciated, since these 150 millisecond positive going pulses are continually applied during the test mode on line 358 to the inputs of gates 360 and 362, the outputs of these gates will be transitioned to a − condition for 150 milliseconds thus causing both the LED's 364 and 366 to conduct and emit light thus performing an effective test of their operational capabilities in the TEST mode.

An alternate partial embodiment employing more digital circuitry is shown in FIG. 15. Here the flip-flops 250, 252 and analogue timers 300, 302 have been effectively replaced with a digital "high counter" and a digital "low counter."

In this embodiment, the lamp inhibit signal on line 106 is preferably shortened to about 25 MS to provide an initial resetting pulse to both the high and low counters as well as a new lamp inhibit latch as shown in FIG. 15.

Input connections to gates G2 and H10 are as previously described in FIG. 7. Circuit elements prior thereto in FIG. 7 are not repeated in FIG. 15 for increased clarity. Accordingly, the output levels of G2 and H10 are as before stated.

Should the initial incoming pulse rate be high, G2 provides no reset pulses for the high counter and both counters thus begin to count the 200 MS pulse signals from H10. Following completion of the second input pulse, the Rate Latch (L1+L2) is initially set for low rate output. Upon completion of the third input pulse, the low counter is reset by the high counter, the rate latch is reset for high rate output and F/F6 output resets the lamp inhibit latch permitting operation of gates H5 and H6.

If the initial incoming pulse rate is low, G2 continuously resets the high counter. Upon completion of the second beat, the Rate latch is set for a low rate output. Upon completion of the third incoming pulse, F/F6 resets the lamp inhibit latch permitting operation of gates H5 and H6.

Should the initial incoming pulses consist of alternate high and low pulses, as can occur in a Bi-Gemini heart condition, it is preferred that the green lamp should come on unless it is superseded by a high rate determination.

In this case, the low counter will count up and since the high counter resets following alternate low rate pulses from G2, the rate latch will set up a low rate output.

Although only a few exemplary embodiments of this invention have been described in detail, those in the art will recognize that there are many possible variations and/or modifictions of the exemplary embodiments which do not depart from the new and improved features of the invention. Accordingly, all such variations or modifications are intended to be included within the scope of this invention.

What is claimed is:

1. Heart monitoring apparatus comprising:
electrodes for electrically contacting a human body,
input signal conditioning means electrically connected to said electrodes for receiving and processing electrical signals taken from said human body, said signals representing the functioning of a heart beating therewithin, said input signal conditioning means including means for detecting each heartbeat cycle and for providing a trigger output pulse for each such heartbeat cycle,
rate detecting means connected to receive said trigger pulses; to provide a high rate output signal if successive trigger pulses are spaced closer in time than a predetermined time interval corresponding to a single predetermined change-over frequency and to provide a low rate output signal if successive trigger pulses are spaced farther in time than said predetermined time interval,
output means operatively connected for selectively providing a high output indication and a low output indication respectively signifying whether the heartbeat rate is higher or lower than said single predetermined change-over frequency,
low-to-high inhibit means operatively connected to said rate detecting means and to said output means for preventing any change from a low output indication to a high output indication unless at least three successive heartbeats occur at a rate higher than said change-over frequency, and
high-to-low inhibit means operatively connected to said rate detecting means and to said output means for preventing any change from a high output indication to a low output indication unless at least two successive heartbeats occur at a rate less than said change-over frequency.

2. Heart monitoring apparatus as in claim 1 wherein said low-to-high inhibit means and said high-to-low inhibit means each comprise an analog time delay circuit means.

3. Heart monitoring apparatus as in claim 1 wherein said low-to-high inhibit means and said high-to-low inhibit means each comprise a digital counting circuit means, 4. Heart monitoring apparatus as in claim 1 further comprising:
a housing having first and second opposingly situated sides,
electrical circuit means comprising the means of claim 1 disposed within said housing for receiving and processing electrical signals taken from a human body, said signals representing the functioning of a heart beating therewithin and including said output means for providing a sensible output indication corresponding to a predetermined characteristic of said electrical signals,
said electrodes comprising first and second electrodes disposed outside said housing adapted for placement at spaced apart areas of a human body,
first and second lead wires respectively connecting said first and second electrodes outside the housing to said electrical input signal conditioning means inside the housing, and
an open-sided storage compartment disposed on the first side of said housing, said compartment having an outer edge sized to receive and holdingly engage said first and second electrodes therewithin in a side-by-side relationship.

5. Heart monitoring apparatus as in claim 4 further comprising:
a wrap-around storage structure means for wrapping and storing said first and second lead wires thereabout, said structure being disposed about the outside perimeter of said storage compartment on the first side of the housing.

6. Heart monitoring apparatus as in claim 5 wherein said first and second lead wires are of different lengths and permanently connected between the housing and the respectively corresponding electrodes to thus facilitate simultaneously storing the wires in said wrap-around storage structure means and storing said electrodes in said open-sided storage compartment on the first side of the housing.

7. Heart monitoring apparatus as in claim 4 further comprising control means disposed on the second side of the housing for selectively controlling the operation of said electrical circuit means.

8. Heart monitoring apparatus as in claim 4 wherein said output means includes means disposed on the second side of the housing for providing said sensible output indications thereat.

9. Heart monitoring apparatus as in claim 4 wherein said electrodes are rectangularly shaped and wherein said open-sided storage compartment is shaped and sized for receiving said electrodes in a flat side-by-side storage configuration on said first side of the housing.

10. Heart monitoring apparatus comprising:
   electrodes for electrically contacting a human body,
   input signal conditioning means electrically connected to said electrodes for receiving and processing electrical signals taken from said human body, said signals representing the functioning of a heart beating therewithin, said input signal conditioning means including means for detecting each heartbeat cycle and for providing a trigger output pulse for each such heartbeat cycle,
   rate detecting means connected to receive said trigger pulses; to provide a high rate output signal if successive trigger pulses are spaced closer in time than a predetermined time interval corresponding to a single predetermined change-over frequency and to provide a low rate output signal if successive trigger pulses are spaced further in time than said predetermined time interval,
   output means operatively connected for selectively providing a high output indication and a low output indication respectively signifying whether the heartbeat rate is higher or lower than said single predetermined change-over frequency,
   low-to-high inhibit means operatively connected to said rate detecting means and to said output means for preventing any change from a low output indication to a high output indication unless at least a first predetermined number of successive heartbeats occur at a rate higher than said change-over frequency,
   high-to-low inhibit means operatively connected to said rate detecting means and to said output means for preventing any change from a high output indication to a low output indication unless at least a second predetermined number of successive heartbeats occur at a rate less than said change-over frequency,
   a housing having first and second opposingly situated sides,
   said input signal conditioning means, said rate detecting means, said output means, said low-to-high inhibit means and said high-to-low inhibit means all being disposed within said housing for receiving and processing electrical signals taken from a human body, said signals representing the functioning of a heart beating therewithin and including said output means for providing a sensible output indication corresponding to a predetermined characteristic of said electrical signals,
   a first electrically conducting area disposed on said first side of the housing,
   a second electrically conducting area disposed on said second side of the housing and electrically insulated from said first conducting area, and
   activation means electrically connected between said first and second electrically conducting areas for activating at least said output means by applying operating power thereto in response to the completion of an electrical circuit between said first and second electrically conducting areas through a human hand when holding said housing therein.

11. Heart monitoring apparatus as in claim 10 wherein:
   said output means disposed within said housing includes means for operating in a plurality of operating modes including a beep mode and an ECG mode and for providing a corresponding plurality of sensible output indications,
   further comprising at least a third electrically conducting area also disposed on said second side of the housing but electrically insulated from said second electrically conducting area, and wherein said activation means is also connected to said third electrically conducting area and including means for selectively activating said means disposed in said housing in a particular one of its operating modes in dependence upon whether said human hand completes an electrical circuit between said first and second electrically conducting areas or between said first and third electrically conducting areas.

12. Heart monitoring apparatus as in claim 11 wherein said output means are also disposed on said second side of the housing so that said sensible output indications can be conveniently observed while the thumb of said hand is selectively placed on said second or third electrically conducting areas to activate said means disposed in said housing in the desired operating mode.

13. Heart monitoring apparatus as in claim 10 wherein one of said first and second electrically conducting areas is electrically connected to a common ground return connection for said means disposed in said housing whereby a human body associated with said hand effectively becomes a source of electrical ground or reference potential when the housing is held in said hand thereby facilitating the elimination of spurious electrical signals in said means disposed in said housing.

14. Heart monitoring apparatus as in claim 13 wherein:
   said electrodes comprise a pair of electrically conducting electrodes for placement at spaced apart areas of the human body and a corresponding pair of lead wires respectively connected thereto and wherein,
   said first electrically conducting area on said first side of the housing comprises a storage compartment for said electrodes and there being a wraparound storage structure for said pair of lead wires provided about the outside perimeter of said storage compartment.

15. Heart monitoring apparatus as in claim 10 wherein said activation means comprises means which consumes less electrical power than that consumed by the rest of said means disposed in said housing by at least a factor of ten.

16. Heart monitoring apparatus as in claim 10 further comprising:
   start-up inhibition means for temporarily inhibiting said output means after the rest of said means disposed in said housing has been activated by said activation means and thus preventing possibly spurious output indications during an initial start-up period.

17. Heart monitoring apparatus comprising:

electrodes for electrically contacting a human body, input signal conditioning means electrically connected to said electrodes for receiving and processing electrical signals taken from said human body, said signals representing the functioning of a heart beating therewithin, said input signal conditioning means including means for detecting each heartbeat cycle and for providing a trigger output pulse for each such heartbeat cycle, rate detecting means connected to receive said trigger pulses; to provide a high rate output signal if successive trigger pulses are spaced closer in time than a predetermined time interval corresponding to a single predetermined change-over frequency and to provide a low rate output signal if successive trigger pulses are spaced further in time than said predetermined time interval, output means operatively connected for selectively providing a high output indication and a low output indication respectively signifying whether the heartbeat rate is higher or lower than said single predetermined change-over frequency, low-to-high inhibit means operatively connected to said rate detecting means and to said output means for preventing any change from a low output indication to a high output indication unless at least a first predetermined number of successive heartbeats occur at a rate higher than said change-over frequency, high-to-low inhibit means operatively connected to said rate detecting means and to said output means for preventing any change from a high output indication to a low output indication unless at least a second predetermined number of successive heartbeats occur at a rate less than said change-over frequency, a battery for supplying electrical energy, a housing including means for carrying said battery therewithin, a self-contained battery operated processing circuit comprising said input signal conditioning means, said rate detecting means, said output means, said low-to-high inhibit means and said high-to-low inhibit means all within said housing for receiving and processing electrical signals taken from a human body, said signals representing the functioning of a heart beating therewithin, and including said output means for providing a sensible output indication corresponding to a predetermined characteristic of said electrical signals, a voltage regulator circuit means disposed within said housing and including means for operative connection with said battery and for supplying a regulated output voltage of predetermined magnitude therefrom to said processing circuit, and battery test means within said housing for temporarily increasing said predetermined magnitude by a predetermined increment and means for sensing the increased magnitude and for thereby indicating a low battery power condition if the battery fails to have enough reserve capacity to supply the temporary demand for an increased regulated voltage output without substantially depleting the battery reserves during the testing process.

18. Heart monitoring apparatus as in claim 17 further comprising:

latch circuit means within said housing operatively connected to said voltage regulator circuit means for automatically inactivating said processing circuit and maintaining it in an inactive state if the regulated output voltage falls below said predetermined magnitude whereby the operation of the battery test means will also automatically inactivate the processing circuit if the battery fails to have enough reserve capacity to supply the temporary demand for an increased regulated voltage output.

19. Heart monitoring apparatus comprising:

a housing having first and second opposingly situated sides, electrodes for electrically contacting a human body, circuit means electrically connected to said electrodes and disposed within said housing for receiving and processing electrical signals taken from said human body via said electrodes, said signals representing the functioning of a heart beating therewithin and including output means for providing a sensible output indication corresponding to a predetermined characteristic of said electrical signals, a first electrically conducting area disposed on said first side of the housing, a second electrically conducting area disposed on said second side of the housing, and activation means electrically connected between said first and second electrically conducting areas for activating said circuit means in response to the completion of an electrical circuit between said first and second electrically conducting areas through a human hand when holding said housing therein.

20. Heart monitoring apparatus as in claim 19 wherein:

said circuit means includes means for operating in a plurality of operating modes including a beep mode and an ECG mode and for providing a corresponding plurality of sensible output indication, further comprising at least a third electrically conducting area also disposed on said second side of the housing but electrically separate from said second electrically conducting area, and wherein said activation means is also connected to said third electrically conducting area and including means for selectively activating said circuit means in a particular one of its operating modes in dependence upon whether said human hand completes an electrical circuit between said first and second electrically conducting areas or between said first and third electrically conducting areas.

21. Heart monitoring apparatus as in claim 20 wherein said output means are also disposed on said second side of the housing so that said sensible output indications can be conveniently observed while the thumb of said hand is selectively placed on said second or third electrically conducting areas to activate said circuit means in the desired operating mode.

22. Heart monitoring apparatus as in claim 19 wherein one of said first and second electrically conducting areas is electrically connected to a common ground return connection for said circuit means whereby a human body associated with said hand effectively becomes a source of electrical ground or reference potential when the housing is held in said hand thereby facilitating the elimination of spurious electrical signals in said circuit means.

23. Heart monitoring apparatus as in claim 22 wherein:
said electrodes comprise a pair of electrically conducting electrodes for placement at spaced apart areas of the human body and a pair of lead wires respectively connected to said electrodes, and
said first electrically conducting area on said first side of the housing comprises a storage compartment for said electrodes and there being a wrap-around storage structure means for said pair of lead wires provided about the outside perimeter of said storage compartment.

24. Heart monitoring apparatus as in claim 19 wherein said activation means includes means for consuming less electrical power than that consumed by said circuit means by at least a factor of ten.

25. Heart monitoring apparatus as in claim 19 further comprising:
start-up inhibition means for temporarily inhibiting said output means after said circuit means has been activated by said activation means and thus preventing possibly spurious output indications during an initial start-up period.

26. Heart monitoring apparatus comprising:
a battery for supplying electrical energy,
a housing including means for carrying said battery therewithin,
a self contained battery operated processing circuit means within said housing for receiving and processing electrical signals taken from a human body, said signals representing the functioning of a heart beating therewithin, and including output means for providing a sensible output indication corresponding to a predetermined characteristic of said electrical signals,
a voltage regulator circuit means including means for operative connection with said battery and means for supplying a regulated output voltage of predetermined magnitude therefrom to said processing circuit means, and
battery test means for temporarily increasing said predetermined magnitude by a predetermined increment including means for sensing the increased magnitude and indicating a low battery power condition if the battery fails to have enough reserve capacity to supply the temporary demand for an increased regulated voltage output without substantially depleting the battery reserves during the testing process.

27. Heart monitoring apparatus as in claim 26 further comprising:
latch circuit means operatively connected to said voltage regulator circuit for automatically inactivating said processing circuit and maintaining it in an inactive state if the regulated output voltage falls below said predetermined magnitude whereby the operation of the battery test means will also automatically inactivate the processing circuit if the battery fails to have enough reserve capacity to supply the temporary demand for an increased regulated voltage output.

28. Heart monitoring apparatus comprising:
a housing having first and second opposingly situated sides,
electrical circuit means disposed within said housing for receiving and processing electrical signals taken from a human body, said signals representing the functioning of a heart beating therewithin and including output means for providing a sensible output indication corresponding to a predetermined characteristic of said electrical signals,
first and second electrodes disposed outside said housing adapted for placement at spaced apart areas of the human body,
first and second lead wires respectively connecting said first and second electrodes outside the housing to said electrical circuit means inside the housing,
an open-sided storage compartment disposed on the first side of said housing, said compartment having an outer edge sized to receive and holdingly engage said first and second electrodes therewithin in a side-by-side relationship, and
a wrap-around storage structure means for wrapping and storing said first and second lead wires thereabout, said structure being disposed about the outside perimeter of said storage compartment on the first side of the housing wherein said first and second lead wires are of different lengths and permanently connected between the housing and the respectively corresponding electrodes to thus facilitate simultaneously storing the wires in said wrap-around storage structure means and storing said electrodes in said open-sided storage compartment on the first side of the housing.

29. Heart monitoring apparatus as in claim 28 further comprising control means disposed on the second side of the housing for selectively controlling the operation of said electrical circuit means.

30. Heart monitoring apparatus as in claim 28 wherein said output means includes means disposed on the second side of the housing for providing said sensible output indications thereat.

31. Heart monitoring apparatus as in claim 28 wherein said electrodes are rectangularly shaped and wherein said open-sided storage compartment includes means for receiving said electrodes in a flat side-by-side storage configuration on said first side of the housing.

32. Heart monitoring apparatus for use by a human user comprising:
a housing adapted in size and shape for holding by a human hand of said user,
two electrodes physically connected via electrical leadwires with said housing, said electrodes being adapted for electrical contact at two respectively corresponding spaced-apart body areas of said human user,
circuit means disposed within said housing for receiving and processing electrical signals taken from the body of said user via said electrodes, said signals representing the functioning of a heart beating within the user's body and including output means for providing a sensible output indication corresponding to a predetermined characteristic of said electrical signals,
said circuit means including at least one differential amplifier means having two differential inputs respectively connected to receive electrical signals from a corresponding one of said electrodes,
said differential amplifier means also having a reference input for providing suppression of common mode noise appearing on said differential inputs when connected with a suitable reference electrical potential, and an electrically conducting area disposed on the outside of the housing in a position normally in contact with said human hand when held thereby, said electrically conducting area constituting a third electrode being electrically connected to said reference input for said circuit means whereby the user's body associated with said hand effectively becomes a source of electrical ground or reference potential when the housing is held in said hand thereby facilitating the suppression of spurious common mode electrical signals in said circuit means from said signals representing the functioning of a heart beating within the user's body.

* * * * *